US009983064B2

(12) United States Patent
Roussev et al.

(10) Patent No.: US 9,983,064 B2
(45) Date of Patent: May 29, 2018

(54) APPARATUS AND METHODS FOR MEASURING MODE SPECTRA FOR ION-EXCHANGED GLASSES HAVING STEEP INDEX REGION

(71) Applicant: CORNING INCORPORATED, Corning, NY (US)

(72) Inventors: Rostislav Vatchev Roussev, Painted Post, NY (US); Vitor Marino Schneider, Painted Post, NY (US)

(73) Assignee: CORNING INCORPORATED, Corning, NY (US)

( * ) Notice: Subject to any disclaimer, the term of this patent is extended or adjusted under 35 U.S.C. 154(b) by 631 days.

(21) Appl. No.: 14/523,171

(22) Filed: Oct. 24, 2014

(65) Prior Publication Data
US 2015/0116713 A1   Apr. 30, 2015

Related U.S. Application Data

(60) Provisional application No. 61/897,546, filed on Oct. 30, 2013.

(51) Int. Cl.
*G01N 21/00* (2006.01)
*G01J 4/02* (2006.01)
(Continued)

(52) U.S. Cl.
CPC .............. *G01J 4/02* (2013.01); *G01N 21/23* (2013.01); *G02B 5/04* (2013.01); *G02B 5/06* (2013.01);
(Continued)

(58) Field of Classification Search
CPC .................................. G01N 21/23; G01J 4/02
See application file for complete search history.

(56) References Cited

U.S. PATENT DOCUMENTS 3,022,181 A   2/1962 Connelly
3,308,394 A   3/1967 Snitzer et al.
(Continued)

FOREIGN PATENT DOCUMENTS

GB   967641 A   10/1961
JP   57157130   9/1982
(Continued)

OTHER PUBLICATIONS

Patent Cooperation Treaty International Notification of Transmittal of the International Search Report and The Written Opinion of the International Searching Authority, international application No. PCT/US2014/062370: dated Feb. 9, 2015, 15 pages.
(Continued)

*Primary Examiner* — Tri Ton
*Assistant Examiner* — Rebecca C Bryant
(74) *Attorney, Agent, or Firm* — Kevin M. Johnson

(57) ABSTRACT

Apparatus and methods for measuring mode spectra for ion-exchanged glass substrates having a steep index region are disclosed. An interfacing fluid is provided between the coupling prism and the glass substrate. The interfacing fluid thickness is selected so that the variation in modal birefringence with fluid thickness is reduced to an acceptable level. The coupling prism can include a prism coating on the coupling surface so that the substrate-prism interface includes the prism coating. The coupling prism can also include stand-off members that serve to define the thickness of the interfacing fluid.

14 Claims, 8 Drawing Sheets

(51) Int. Cl.
*G02B 5/04* (2006.01)
*G02B 5/06* (2006.01)
*G02B 6/34* (2006.01)
*G01N 21/23* (2006.01)
*G01J 4/00* (2006.01)
*G01N 21/43* (2006.01)
*G01N 21/41* (2006.01)

(52) U.S. Cl.
CPC .......... *G02B 6/34* (2013.01); *G01J 2004/005* (2013.01); *G01N 21/43* (2013.01); *G01N 2021/4126* (2013.01); *G01N 2021/434* (2013.01)

(56) References Cited

U.S. PATENT DOCUMENTS

| | | | |
|---|---|---|---|
| 3,433,611 A | 3/1969 | Saunders et al. | |
| 3,873,209 A | 3/1975 | Schinke et al. | 356/135 |
| 3,883,221 A | 5/1975 | Rigrod | 350/96 |
| 3,941,605 A | 3/1976 | Yamashita | |
| 4,207,000 A | 6/1980 | Miller | |
| 4,353,649 A | 10/1982 | Kishii | |
| 4,637,684 A | 1/1987 | Tomita et al. | 350/96.19 |
| 4,655,589 A | 4/1987 | Cestaro et al. | |
| 5,164,589 A | 11/1992 | Sjodin | |
| 5,446,534 A | 8/1995 | Goldman | |
| 5,674,790 A | 10/1997 | Araujo | |
| 5,953,125 A | 9/1999 | de Groot | |
| 6,459,492 B1 | 10/2002 | Hercher | |
| 6,498,118 B1 | 12/2002 | Landa et al. | |
| 6,716,780 B2 | 4/2004 | Landa et al. | |
| 6,731,388 B1 | 5/2004 | Simon et al. | |
| 7,193,719 B2 | 3/2007 | Meehan et al. | |
| 7,407,902 B2 | 8/2008 | Hasegawa et al. | |
| 7,701,529 B2 | 4/2010 | Kogure et al. | |
| 8,281,510 B2 | 10/2012 | Yoshimura et al. | |
| 8,957,374 B2 | 2/2015 | Liu et al. | |
| 9,109,881 B2 | 8/2015 | Roussev et al. | |
| 9,140,534 B2 | 9/2015 | Manley | |
| 9,140,543 B1 | 9/2015 | Allan et al. | |
| 2010/0028607 A1 | 2/2010 | Lee et al. | |
| 2011/0171746 A1 | 7/2011 | Fontaine et al. | |
| 2012/0106164 A1 | 5/2012 | Michaelis et al. | |
| 2012/0257387 A1 | 10/2012 | Kuchibhotla et al. | |
| 2013/0147179 A1 | 6/2013 | Baloukas et al. | |
| 2014/0092377 A1 | 4/2014 | Liu et al. | 356/51 |
| 2014/0118740 A1 | 5/2014 | Fontaine et al. | |
| 2014/0368808 A1 | 12/2014 | Roussev et al. | 356/32 |
| 2015/0066393 A1 | 3/2015 | Liu et al. | |
| 2015/0116713 A1 | 4/2015 | Roussev et al. | |
| 2015/0338308 A1 | 11/2015 | Li et al. | |

FOREIGN PATENT DOCUMENTS

| | | |
|---|---|---|
| JP | 04310836 | 11/1992 |
| JP | H04310836 A | 11/1992 |
| JP | 11281501 | 10/1999 |
| JP | 2002131224 | 5/2002 |

OTHER PUBLICATIONS

Chiang, "Refractive-Index Profiling of Graded-Index Planar Waveguides from Effective Indexes Measured with Different External Refractive Indexes." Journal of Lightwave Technology, vol. 18, No. 10, Oct. 2000.
Chiang, "Refractive-Index Profiling of Buried Planar Waveguides by an Inverse Wentzel-Kramer-Brillouin Method." Journal of Lightwave Technology, vol. 26, No. 11, Jun. 1, 2008.
Pitt and Walpita, "Lightguiding in Langmuir-Blodgett Films." Thin Solid Films, 68 (1980) 101-127.
Ulrich, "Theory of the Prism-Film Coupler by Plane-Wave Analysis." Journal of the Optical Society of America, vol. 60 No. 10, 1337-1350.
Surface Stress Meter FSM-60 Manual, Orihara Industrial Co.
Surface Stress Meter FSM-6000 Manual, Orihara Industrial Co.
Metricon 2010 manual, Metricon corporation.
F. Zernike, J.E. Midwinter, "Improved Version of the Evanescent=Wave Coupler", IEEE Journal of Quantum Electronics, Sep. 1970, pp. 577-578.
P.K. Tien, "Light waves in thin films and integrated optics", Applied Optics 10, p. 2395 (1971).
P.K. Tien and R. Ulrich, "Theory of Prism-Film Coupler and Thin-Film Light Guides", Journal of the Optical Society of America 60, p. 1325 (1970).
Agan et al; "Stress effects in prism coupling measurements of thin polymer films"; App. Phys. A 80, 341-345 2005.
Brandenburg; "Stress in ion-exchanged glass waveguides"; Journal of Lightwave Technology, vol. LT4, No. 10, Oct. 1986.
Invitation to Pay Additional Fees; PCT/US2015/066022; dated Apr. 5, 2016.
Kishii, "Surface stress meters utilizing the optical waveguide effect of chemically tempered glasses", Optics and Lasers in Engineering, vol. 4, pp. 25-38 (1983).
McRae et al; "The measurement of compression stress in eggshells"; Journal of Agricultrual Engineering Research, vol. 14, No. 1, Mar. 1, 1969.
PCT/2014/062370 Search Report dated Feb. 9, 2015.
PCT/US2014/053069 Search Report dated Dec. 9, 2014.
Pelletier et al; "Optical characterization of thin films by guided waves"; Applied Optics; vol. 28, No. 14, Jul. 1989 pp. 2918-2924.
Rau et al; "Prism coupled Terahertz waveguide sensor"; Applied Physics Letters, 86, 211119 (2005).
Ulrich et al.; "Measurement of Thin Film Parameters with a Prism Coupler"; Applied Optics, vol. 12, No. 12 (Dec. 1973); pp. 2901-2908.

APPARATUS AND METHODS FOR MEASURING MODE SPECTRA FOR ION-EXCHANGED GLASSES HAVING STEEP INDEX REGION

CROSS-REFERENCE TO RELATED APPLICATIONS

This application claims the benefit of priority under 35 U.S.C. § 119 of U.S. Provisional Application Ser. No. 61/897,546, filed on Oct. 30, 2013, the content of which is relied upon and incorporated herein by reference in its entirety.

BACKGROUND

The present disclosure relates to characterizing ion-exchanged glasses, and in particular relates to apparatus and methods for measuring mode spectra for ion-exchanged glasses having a steep and shallow near-surface refractive index region.

Certain types of glasses and glass-ceramics can be chemically strengthened by an ion exchange process. The strengthening is due to the formation of a near-surface compression layer that usually creates stress-induced birefringence. The birefringence in turn corresponds to a polarization-dependent change in refractive index profile in the glass. The ion exchange process typically alters the refractive index profile with a shape that corresponds to the concentration of the ions diffused into the glass. The stress and the birefringence are linearly related through the stress optic coefficient.

There is increasing commercial interest in chemically strengthened glasses with anti-microbial (AM) surface properties. Such glasses can be fabricated using a double ion-exchange (DIOX) process wherein a first ion exchange (IOX) process is performed for strengthening. The IOX process involves a larger alkali ion such as $K^+$ that exchange for a smaller alkali ion, such as $Na^+$ or $Li^+$ present in the original base (bulk) glass. The first IOX process is followed by a second IOX process that includes an anti-microbial ion, such as $Ag^+$. In some cases, both exchanging ions (i.e., larger alkali ions and anti-microbial ions) can be supplied simultaneously. The resulting refractive index profile includes a steep and shallow near-surface region followed by a less-steep and deeper region.

Optical methods of characterizing ion-diffused glasses using prism coupling and the analysis of the resulting mode spectra are known in the art. However, prior-art prism-coupling systems and methods cannot adequately measure the mode spectra of steep and shallow near-surface regions of a refractive-index profile.

In particular, in the prior art, the range of refractive index obtained through chemically strengthening ion exchange and measured by high-resolution mode-spectra measurement systems is usually less than about 0.02 RIU (refractive-index units). This limited range allows prior art systems and methods to take advantage of a linear approximation between the measured mode spectra positions at the photodetector and the mode effective index. However, as the index profiles attributable to anti-microbial glass often have a range of refractive index exceeding or substantially exceeding 0.03 RIU, the linear approximation becomes less accurate and leads to systematic errors in the calculated index and stress profiles, especially at and near the substrate surface.

Even more importantly, prior-art systems for measuring stress cannot detect the optical modes of propagation in the steep near-surface region of the index profile, or in some cases cannot detect them with adequate precision for practically useful stress measurements. A different-type prism-coupling system based on a laser source and using a rotating prism and piston applied to the substrate can be used to detect the modes of the shallow and steep index of the index profile, but they do not have the precision needed for stress measurement, nor the resolution to properly resolve the some of the modes that propagate primarily in the less-steep and deeper region of the refractive index profile.

SUMMARY

A first aspect of the disclosure is a method of measuring TM and TE mode spectra of an ion-exchanged glass substrate having a bulk refractive index $n_s$, a surface and a refractive index profile with a steep and shallow near-surface region R1. The method includes: interfacing a coupling prism of refractive index $n_p$ to the substrate surface to define a prism-substrate interface, with an interfacing fluid of refractive index $n_f$ and thickness d1 residing between the coupling prism and substrate surface, wherein $n_f \leq n_s < n_p$, wherein region R1 satisfies $$\left| \frac{\lambda}{n} \frac{dn}{dx} \right| \geq 0.0004,$$

wherein $\lambda$ is a measurement wavelength of measuring light; wherein the TM and TE mode spectra each include first and second lowest-order modes (i.e., a fundamental mode and the next-highest-order mode), and selecting the thickness d1 to be within a thickness range such that that mode birefringence of at least the first and second lowest-order modes of the TM and TE mode spectra as measured in the presence of the coupling prism remains substantially unchanged within the thickness range; and directing the measuring light through the coupling prism and through the interfacing fluid into the substrate surface and digitally capturing TE and TM mode spectra reflected from the prism-substrate interface.

Another aspect of the disclosure is a method of measuring TM and TE mode spectra of an ion-exchanged glass substrate having a bulk refractive index $n_s$, a surface and a refractive index profile with a steep and shallow near-surface region R1. The method includes: interfacing a coupling prism of refractive index $n_p$ to the substrate surface to define a prism-substrate interface, with the coupling prism having a coupling surface with a coating of thickness d2 and refractive index $n_c$ wherein $0.2\lambda \leq n_c \cdot d2 \leq 0.8\lambda$; providing an interfacing fluid of refractive index $n_f$ and thickness d1 between the prism coating and substrate surface, wherein $n_c \leq n_f \leq n_s < n_p$, wherein region R1 satisfies $$\left| \frac{\lambda}{n} \frac{dn}{dx} \right| \geq 0.0004,$$

wherein $\lambda$ is a measurement wavelength of measuring light; and directing the measuring light through the coupling prism and through the interfacing fluid into the substrate surface and digitally capturing TE and TM mode spectra reflected from the prism-substrate interface.

Another aspect of the disclosure is a coupling prism for a prism coupling system for measuring mode spectra of an ion-exchanged waveguide having a refractive index $n_s$ and a surface. The coupling prism includes: a coupling prism body having a refractive index $n_p$ and an input surface, an output surface and a coupling surface; and a prism coating on the coupling surface, the prism coating having a thickness d2 and refractive index $n_c$ wherein $0.2\lambda \leq n_c \cdot d2 \leq 0.8\lambda$.

Additional features and advantages are set forth in the Detailed Description that follows, and in part will be readily apparent to those skilled in the art from the description or recognized by practicing the embodiments as described in the written description and claims hereof, as well as the appended drawings. It is to be understood that both the foregoing general description and the following Detailed Description are merely exemplary, and are intended to provide an overview or framework to understand the nature and character of the claims.

BRIEF DESCRIPTION OF THE DRAWINGS

The accompanying drawings are included to provide a further understanding, and are incorporated in and constitute a part of this specification. The drawings illustrate one or more embodiment(s), and together with the Detailed Description serve to explain principles and operation of the various embodiments. As such, the disclosure will become more fully understood from the following Detailed Description, taken in conjunction with the accompanying Figures, in which.

Cartesian coordinates are shown in some of the Figures for ease of illustration and discussion and are not intended to be limiting as to direction or orientation.

DETAILED DESCRIPTION

Reference is now made in detail to various embodiments of the disclosure, examples of which are illustrated in the accompanying drawings. Whenever possible, the same or like reference numbers and symbols are used throughout the drawings to refer to the same or like parts. The drawings are not necessarily to scale, and one skilled in the art will recognize where the drawings have been simplified to illustrate the key aspects of the disclosure.

The claims as set forth below are incorporated into and constitute part of this Detailed Description.

The entire disclosure of any publication or patent document mentioned herein is incorporated by reference, including U.S. patent application Ser. No. 13/463,322, entitled "Systems and methods for measuring the stress profile of ion-exchanged glass," U.S. Provisional Patent Application Ser. No. 61/706,891, entitled "Systems and methods for measuring birefringence in glass and glass-ceramics," and U.S. Provisional Patent Application Ser. No. 61/835,823, entitled "Prism coupling methods with improved mode spectrum contrast for double ion-exchanged glass."

Figure 1A:
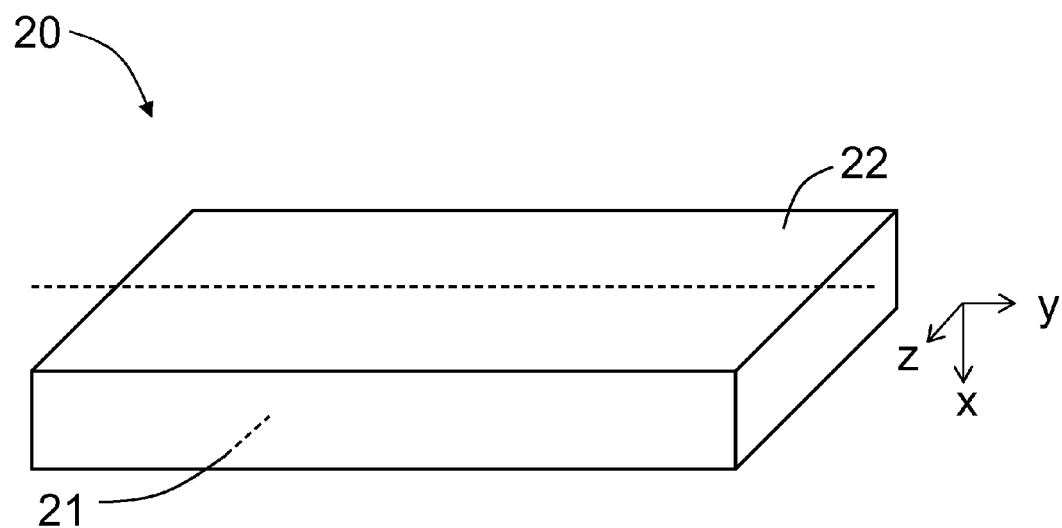
FIG. 1A is an elevated view of an example DIOX glass substrate in the form of a planar substrate.
Figure 1B:
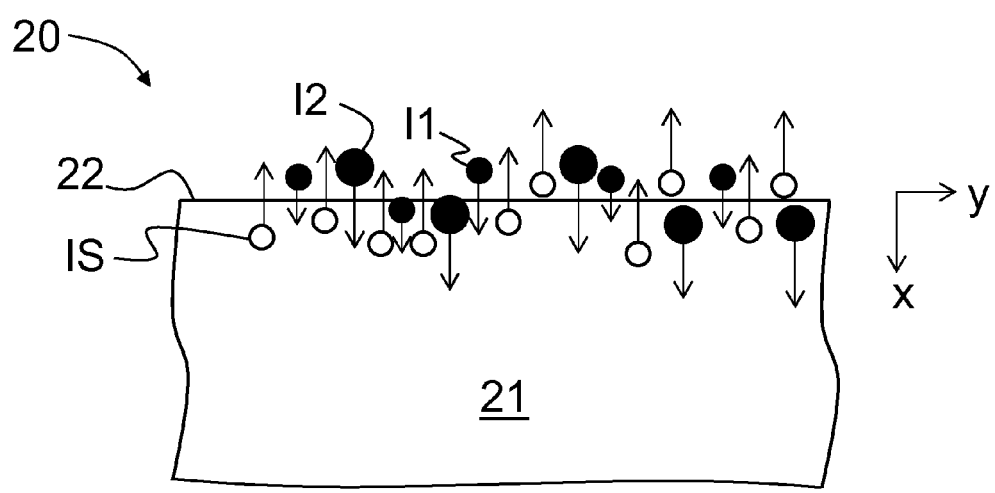
FIG. 1B is a close-up cross-sectional view of the DIOX substrate of FIG. 1A as taken in the x-y plane and that illustrates the double ion-exchange process that takes place across the substrate surface and into the body of the substrate.

FIG. 1A is an elevated view an example glass substrate in the form of a planar ion-exchanged substrate 20 that has a body 21 and a (top) surface 22, wherein the body has a base (bulk) refractive index $n_s$ and a surface refractive index $n_0$. FIG. 1B is a close-up cross-sectional view of substrate 20 as taken in the x-y plane and illustrates an example double ion-exchange (DIOX) process that takes place across surface 22 and into body 21 in the x-direction.

Figure 1C:
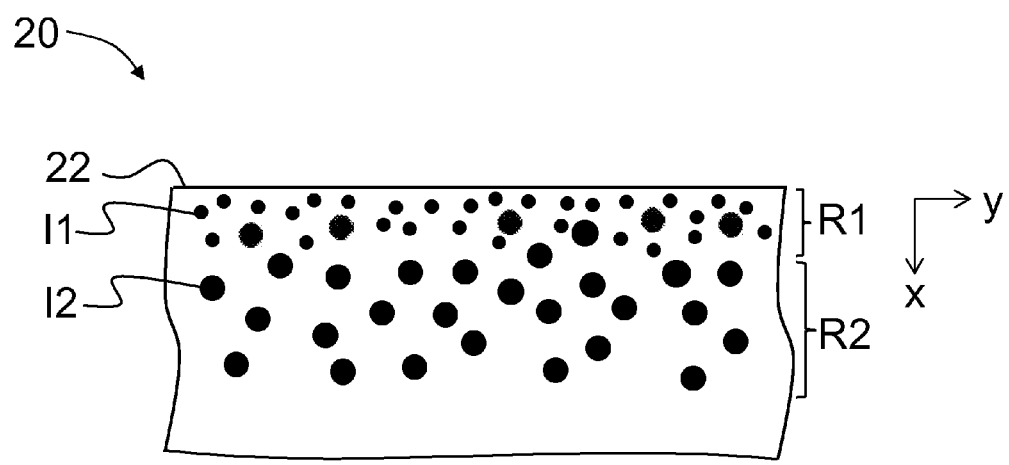
FIG. 1C schematically illustrates the result of the DIOX process that forms the DIOX substrate.

FIG. 1C schematically illustrates the result of the double ion-exchange process that forms ion-exchanged substrate 20. The ion-exchanged substrate 20 includes substrate ions IS in body 21 that exchange for first ions I1 and second ions I2. The first and second ions I1 and I2 can be introduced into the glass body either sequentially or concurrently using known techniques. For example, second ions I2 can be $K^+$ ions introduced via a $KNO_3$ bath for strengthening, prior introducing first ions I1 that can be $Ag^+$ ions subsequently introduced via a $AgNO_3$ bath to add the anti-microbial property adjacent surface 22. The circles in FIG. 1B that represent ions I1 and I2 are used for schematic illustration only, and their relative sizes do not necessarily represent any actual relationship between the sizes of the actual ions participating in the ion exchange.

In addition, ions I1 may be present in significant numbers in both regions R1 and R2, as may be ions of type I2. Even with a one-step ion-exchange process it is possible to observe the formation of two regions R1 and R2, with significant differences in the relative concentrations of ions I1 and I2. In an example, using an ion exchange of Na-containing glass in a bath containing a mixture of $KNO_3$ and $AgNO_3$, it is possible to obtain a region R1 with significant concentration of both $Ag^+$ and $K^+$, and region R2 also with significant concentration of $Ag^+$ and $K^+$, but the relative concentration of $Ag^+$ with respect to $K^+$ may be significantly larger in region R1 compared to region R2.

Figure 2:
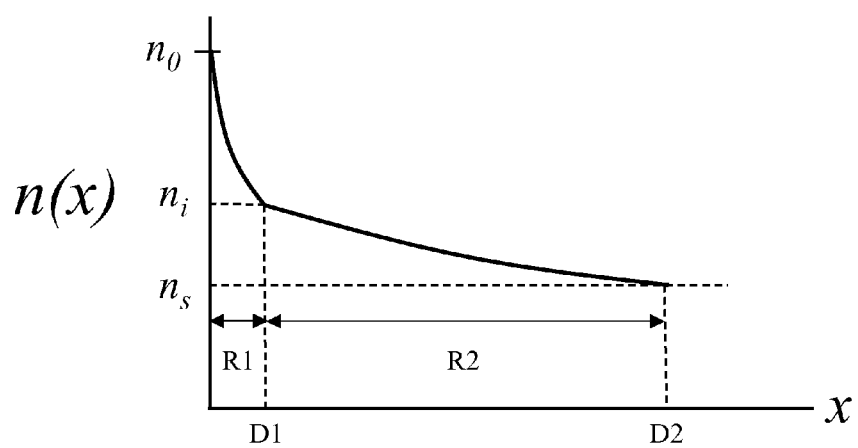
FIG. 2 is a representation of an example refractive index profile n(x) for the DIOX substrate illustrated in FIG. 1C.

FIG. 2 is a representation of an example refractive index profile n(x) for ion-exchanged substrate 20 such as illustrated in FIG. 1C. The refractive index profile n(x) includes a first region R1 associated with the shallower ion-exchange (ions I1) and has depth D1 into body 21. The refractive index profile n(x) has a second region R2 associated with the deeper ion-exchange (ions I2) that has a depth D2. The deeper region may be produced in practice prior to the shallower region. Region R1 is adjacent substrate surface 22 and is relatively steep and shallow (e.g., D1 is a few microns), whereas region R2 is less steep and extends relatively deep into the substrate (e.g., D2 can be about 20-50 microns). In an example, region R1 has a maximum refractive index $n_0$ at substrate surface 22 and steeply tapers off to an intermediate index $n_i$, while region R2 tapers more gradually from the intermediate index $n_i$ down to the substrate (bulk) index $n_s$. It is emphasized here that other ion-exchanged processes can result in a steep and shallow near-surface refractive index change, and that a double ion-exchange process is discussed here by way of illustration.

In an example, the methods disclosed herein employ optical measurements of ion-exchanged substrate 20 using a prism coupling system as described below. Such systems are generally known in the art, and example systems suitable for use in carrying out the methods of the present disclosure with the modifications set forth below are described in U.S. patent application Ser. No. 13/463,322, entitled "Systems and methods for measuring the stress profile of ion-exchanged glass," and in U.S. Patent Application Ser. No. 61/706,891 entitled "Systems and methods for measuring birefringence in glass and glass-ceramics."

Prior art prism coupling systems have great difficulty resolving with high precision the TM and TE mode spectra for the near-surface index region R1 that has a steep and shallow refractive index profile with steepness characterized by the condition $$\left|\frac{\lambda}{n}\frac{dn}{dx}\right| \geq 0.0004,$$

particularly when $$\left|\frac{\lambda}{n}\frac{dn}{dx}\right| \geq 0.0005,$$

and especially when $$\left|\frac{\lambda}{n}\frac{dn}{dx}\right| \geq 0.0008.$$

The index profile n(x) generally decreases with increasing depth x, although it may have some regions where the index is flat, or even increases with increasing depth. For example, there may be a very shallow region (e.g., 100 nm), substantially thinner than the optical wavelength in the glass, where the index profile n(x) may be increasing with depth x before it starts decreasing at larger depths.

In example embodiments, the systems and methods disclosed herein are applied to $$\left|\frac{\lambda}{n}\frac{dn}{dx}\right| \geq 0.0004 \text{ or } \left|\frac{\lambda}{n}\frac{dn}{dx}\right| \geq 0.0005,$$

a near-surface region R1 (see FIG. 4B) that satisfies the condition $$\left|\frac{\lambda}{n}\frac{dn}{dx}\right| \geq 0.0008.$$

and in other embodiments, satisfies the condition

The TM and TE mode spectra are difficult to resolve due to substantial broadening and associated decrease in contrast of the coupling resonances (i.e., spectral lines or mode lines). This broadening is believed to be due to the excessive coupling between the modes and coupling prism 40 as mediated by interfacing fluid 52, and the "leaky" nature of the modes. In particular, the low-order modes, which are confined close to substrate top surface 22, experience more bounces at the surface per unit propagation length than higher-order modes. Consequently, these modes lose their energy much more quickly with propagation, experiencing substantial losses due to refraction of part of the light into the interfacing fluid 52 and coupling prism 40 (and out of the wave-guiding region R1) at every bounce.

This makes processing the TE and TM mode spectra for ion-exchanged substrate 20 problematic when trying to apply the prior art measurement methods. Also, the diminished mode-spectra contrast also renders problematic the calculating of the birefringence using methods for extraction of the TE and TM index profiles, including but not limited to the inverse Wentzell-Kramers-Brillouin (IWKB) method, and in fact produces incorrect results for the stress, as well as the depth of layer (DOL).

Prism Coupling System

Figure 3A:
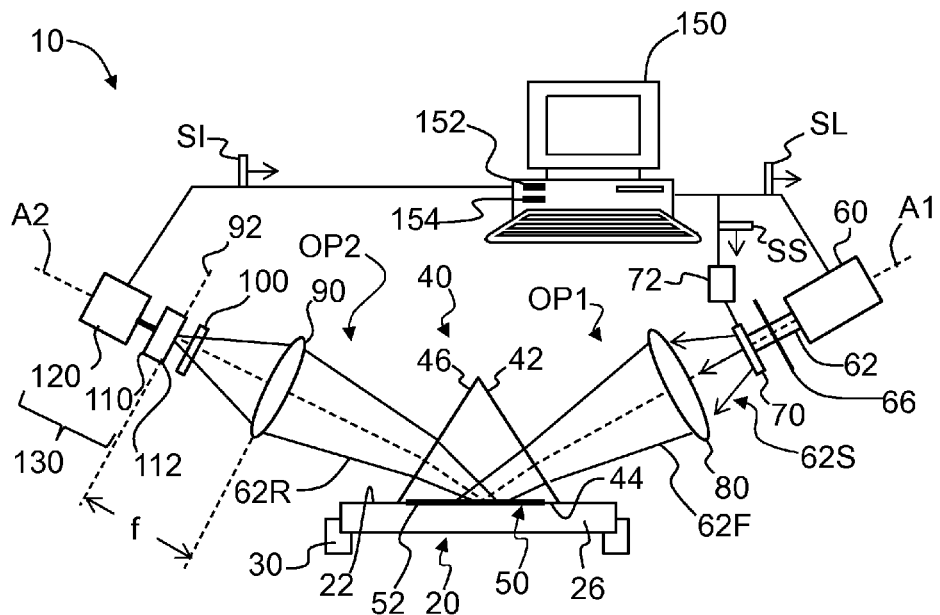
FIG. 3A is a schematic diagram of an example prism-coupling system according to the disclosure.

FIG. 3A is a schematic diagram of an example prism-coupling system ("system") 10 suitable for carrying out the methods of measuring the TE and TM mode spectra for ion-exchanged substrate 20 as disclosed herein, containing the steep and shallow near-surface region R1. In an example, ion-exchanged substrate 20 constitutes a chemically strengthened glass such as GORILLA® glass, made by Corning, Inc., of Corning, N.Y.

The system 10 includes a substrate holder 30 configured to hold substrate 20. In alternative embodiments, however, substrate holder 30 is not required. System 10 also includes coupling prism 40 that includes an input surface 42, a coupling surface 44 and an output surface 46. The coupling prism 40 has a refractive index $n_p > n_s$. The coupling prism 40 is interfaced with substrate 20 by bringing coupling-prism coupling surface 44 and substrate top surface 22 into optical contact, thereby defining a substrateprism interface ("interface") 50 that includes an interfacing fluid 52. Details of how coupling prism 40 is interfaced with ion-exchanged substrate 20 are discussed below.

In an example embodiment, coupling prism 40 has a trapezoidal, curved or other cross-sectional shape instead of the triangular cross-sectional shape that is shown in FIG. 3A by way of illustration. The term "curved" here refers to cases where the input surface 42 and/or output surface 46 may be curved, such as cylindrical or spherical surfaces.

With continuing reference to FIG. 3A, system 10 includes optical axes A1 and A2 that respectively pass through input and output surfaces 42 and 46 of coupling prism 40 to generally converge at interface 50 after accounting for refraction at the prism/air interfaces. The system 10 includes, in order along axis A1, a light source 60 that emits measuring light 62 of wavelength, an optional optical filter 66 that may be alternatively included in the detector path on axis A2, an optional light-scattering element 70 that forms scattered light 62S, and an optional focusing optical system 80 that forms focused (measuring) light 62F, as explained below. Thus, in an example of system 10, there are no optical elements between light source 60 and prism input surface 42.

The system 10 also includes, in order along axis A2 from coupling prism 40, a collection optical system 90 having a focal plane 92 and a focal length f and that receives reflected light 62R as explained below, a TM/TE polarizer 100, and a photodetector system 130. The axis A1 defines the center of an optical path OP1 between light source 60 and coupling-prism coupling surface 44. The axis A2 defines the center of an optical path OP2 between coupling surface 44 and photodetector system 130. Note that axes A1 and A2 may be bent at input and output surfaces 42 and 46, respectively, due to refraction. They may also be broken into sub-paths by insertion of mirrors in optical paths OP1 and/or OP2.

Figure 3B:
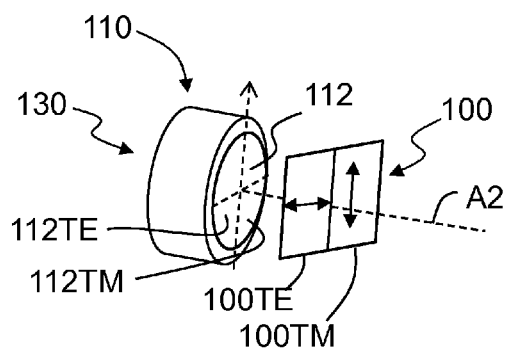
FIG. 3B is a close-up view of the photodetector system of the prism-coupling system of FIG. 3A.

In an example, photodetector system 130 includes a detector (camera) 110 and a frame grabber 120. In other embodiments discussed below, photodetector system 130 includes a CMOS or CCD camera. FIG. 3B is a close-up elevated view of the TM/TE polarizer and detector 110 of photodetector system 130. The photodetector system 130 includes a photosensitive surface 112. The photosensitive surface 112 resides in focal plane 92 of collecting optical system 90, with the photosensitive surface being generally perpendicular to axis A2. This serves to convert the angular distribution of reflected light 62R exiting the coupling prism output surface 46 to a transverse spatial distribution of light at the sensor plane of camera 110. In an example embodiment, photosensitive surface 112 comprises pixels, i.e., detector 110 is a digital detector, e.g., a digital camera.

Figure 3C:
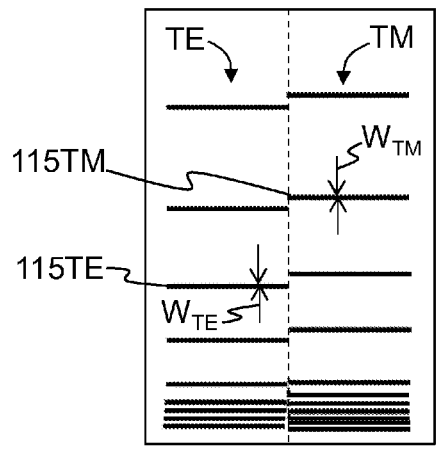
FIG. 3C is a schematic representation of TM and TE mode spectra as captured by the photodetector system of FIG. 3B.

Splitting photosensitive surface 112 into TE and TM sections 112TE and 112TM allows for the simultaneous recording of digital images of the angular reflection spectra (mode spectra) for the TE and TM polarizations of reflected light 62R. This simultaneous detection eliminates a source of measurement noise that could arise from making the TE and TM measurements at different times, given that system parameters can drift with time. FIG. 3C is a schematic representation of TM and TE mode spectra as captured by photodetector system 130. The TM and TE mode spectra are made up of respective spectral lines 115TM and 115TE having respective widths $W_{TM}$ and $W_{TE}$ as explained in greater detail below.

Example light sources 60 include lasers, light-emitting diodes, and broader-bandwidth sources such as hot-filament lamps and quartz lamps. Example operating wavelengths λ of light 62 generated by light source 60 can include near-ultra-violet, visible and infrared wavelengths.

The system 10 includes a controller 150, which is configured to control the operation of the system. The controller 150 is also configured to receive and process image signals SI from photodetector system 130 that are representative of captured TE and TM mode spectra images. The controller 150 includes a processor 152 and a memory unit ("memory") 154. The controller 150 may control the activation and operation of light source 60 via a light-source control signal SL, and receives and processes image signals SI from photodetector system 130 (e.g., from frame grabber 120, as shown).

In an example, controller 150 comprises a computer and includes a reading device, for example, a floppy disk drive, a CD-ROM drive, a DVD drive, a magnetic optical disk (MOD) device (not shown), or any other digital device including a network-connecting device, such as an Ethernet device (not shown), for reading instructions and/or data from a computer-readable medium, such as a floppy disk, a CD-ROM, a DVD, a MOD, a flash drive, or another digital source such as a network or the Internet. The controller 150 is configured to execute instructions stored in firmware and/or software (not shown), including signal-processing instructions for carrying out the surface birefringence/stress measurements disclosed herein. In examples, the terms "controller" and "computer" are interchangeable.

The controller 150 is programmable to perform the functions described herein, including the operation of system 10 and the aforementioned signal processing of image signals SI in order to arrive at a measurement of the stress characteristics of substrate 20, such as the stress profile S(x), birefringence, or compressive stress CS. As used herein, the term "computer" is not limited to just those integrated circuits referred to in the art as computers, but broadly refers to computers, processors, microcontrollers, microcomputers, programmable logic controllers, application-specific integrated circuits, and other programmable circuits, and these terms are used interchangeably herein.

Software may implement or aid in the performance of the operations of system 10 disclosed herein, including the aforementioned signal processing. The software may be operably installed in controller 150 and in particular in processor 152 and memory 154. Software functionalities may involve programming, including executable code, and such functionalities may be used to implement the methods disclosed herein. Such software code is executable by the general-purpose computer or by the processor unit described below.

In operation, the code and possibly the associated data records are stored within a general-purpose computer platform, within processor 152 and/or in memory 154. At other times, however, the software may be stored at other locations and/or transported for loading into the appropriate general-purpose computer systems. Hence, the embodiments discussed herein involve one or more software products in the form of one or more modules of code carried by at least one machine-readable medium. Execution of such code by processor 152 of computer system 150 or by the processor unit enables the platform to implement the catalog and/or software downloading functions in essentially the manner performed in the embodiments discussed and illustrated herein.

The controller 150 and/or processor 152 may each employ a computer-readable medium or machine-readable medium (e.g., memory 154), which refers to any medium that participates in providing instructions to the processor for execution, including, for example, determining an amount of surface birefringence/stress or the stress profile S(x) of substrate 20. The memory 154 constitutes a computer-readable medium. Such a medium may take many forms, including but not limited to non-volatile media, volatile media and transmission media. Non-volatile media include, for example, optical or magnetic disks, such as any of the storage devices in any computer(s) operating as one of the server platforms discussed above. Volatile media include dynamic memory, such as the main memory of such a computer platform. Physical transmission media include coaxial cables, copper wire and fiber optics, including the wires that comprise a bus within a computer system.

Common forms of computer-readable media therefore include, for example, a floppy disk, a flexible disk, a hard disk, magnetic tape, flash drives and any other magnetic medium; a CD-ROM, a DVD and any other optical medium; less commonly used media such as punch cards, paper tape and any other physical medium with patterns of holes; a RAM, a PROM, an EPROM, a FLASH-EPROM and any other memory chip or cartridge; a carrier wave transporting data or instructions, cables or links transporting such a carrier wave, or any other medium from which a computer can read programming code and/or data. Many of these forms of computer-readable media may be involved in carrying one or more sequences of one or more instructions to processor 152 for execution.

In an example, controller 150 is programmed to determine at least one characteristic of ion-exchanged substrate 10 based on the measured mode spectra. Example characteristics include: surface stress, stress profile, compressive stress, depth of layer, refractive index profile, and birefringence. In an example, controller 150 is programmed to carry out calculations as disclosed in the article by A. Brandenburg, "Stress in Ion-Exchanged Glass Waveguides," Journal of Lightwave Technology, Vol. LT-4, No. 10, October 1986, pp. 1580-93.

System 10 may be a modified version of a commercial prism-coupling instrument, such as the FSM-6000 prism-coupling instrument made and sold by Orihara Industrial Co., Ltd., of Tokyo, Japan. The FSM-6000 instrument represents the state of the art in high-throughput non-destructive measurements of stress in flat ion exchanged glasses, and utilizes a coupling prism 40 with a prism index $n_p$=1.72 at 589 nm. The FSM-6000 uses an index-matching fluid having an index $n_f$=1.64. In the FSM-6000 instrument, the surface compressive stress (CS) is calculated from the effective indices $n_{eff}$ of the first two transverse magnetic (TM) and the first two transverse electric (TE) modes, while the total number of observed modes is used along with the substrate index and the aforementioned effective indices of the first 2 modes for the depth of layer (DOL) calculation based on a linear refractive-index profile assumption.

Interfacing Fluid

Figure 4A:
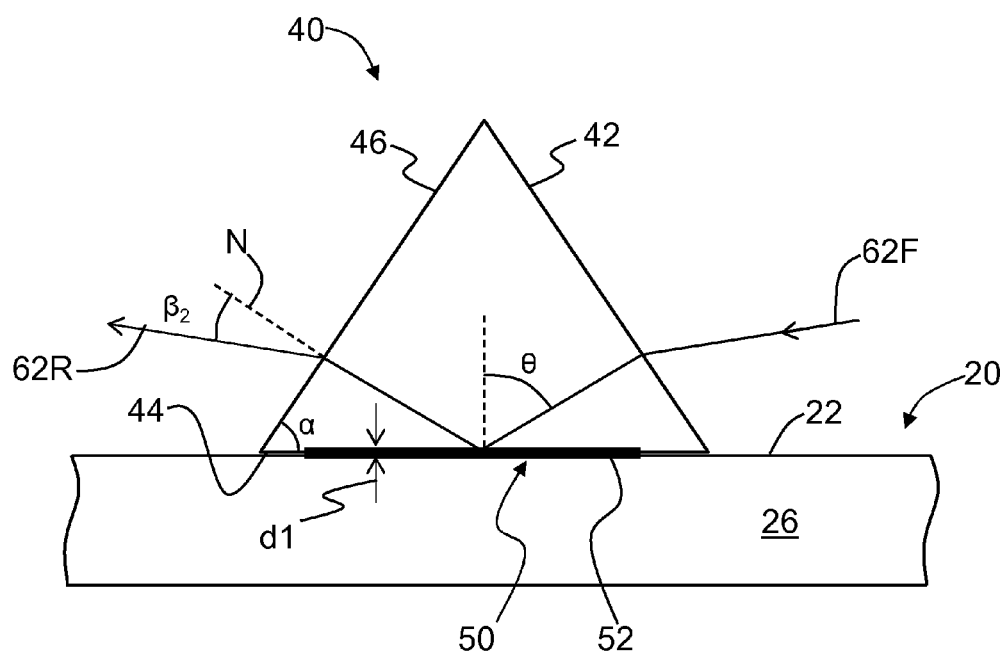
FIG. 4A is a close-up view of an example coupling prism interfaced with the ion-exchanged substrate using an interfacing fluid having a thickness d1 and a refractive index $n_f$.

FIG. 4A is a close-up cross-sectional view of coupling prism 40 as interfaced with ion-exchanged substrate 20 using interfacing fluid 52. The coupling prism angle α is shown, along with the coupling angle θ, exit angle $β_2$ and surface normal N. Interfacing fluid 52 has a thickness d1 and the aforementioned fluid index $n_f$. An example type of interfacing fluid is oil, such as index-matching oil.

Figure 4B:
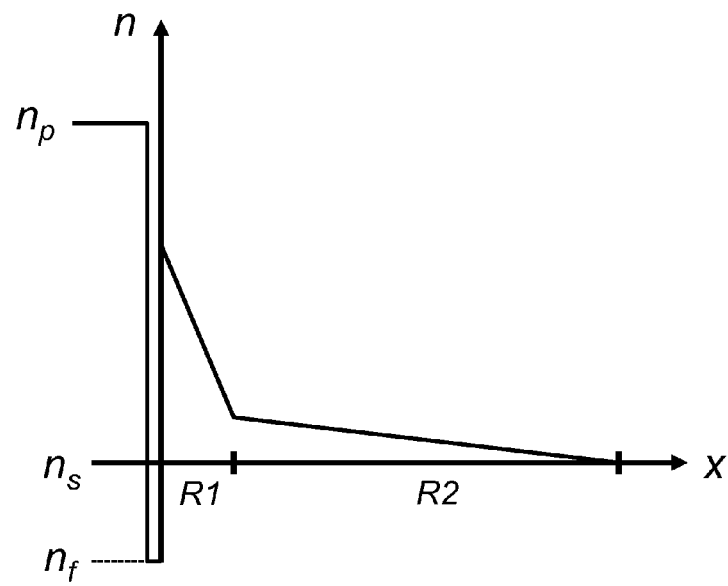
FIG. 4B is a plot of the refractive index profile n vs. distance x for the coupling prism, interfacing fluid and substrate, which includes a shallow and steep near-surface index region R1 followed by a deeper and less-steep index region R2.

FIG. 4B is a plot of refractive index n as a function of x, wherein x=0 represents the top surface 22 of ion-exchanged substrate 20. The plot of FIG. 4B represents an example refractive index structure for coupling prism 40, interfacing fluid 52 and ion-exchanged substrate 20. The indices of refraction for coupling prism 40 ($n_p$), interfacing fluid 52 ($n_f$) and ion-exchanged substrate ($n_s$) satisfy the condition $n_f < n_s < n_p$, for $n_p > n_{eff}$ and $n_f < n_{eff}$, wherein $n_{eff} = n_p \cdot \sin(θ)$ is the effective index for the mode associated with the given angle θ. For these conditions, system 10 can produce dark-line prism-coupling TM and TE mode spectra having improved contrast and reduced linewidth for the lowest-order modes as compared to the conventional configuration of system 10. The interfacing fluid index $n_f$ should be lower than the lowest of the effective mode indices sought to be measured.

If all guided modes are to be observed with high contrast, then $n_f$ should be lower than all of the effective indices to be measured. In an example, $n_f$ should be lower than the bulk refractive index of the glass $n_s$, which represents an approximate lower bound for the effective indices of all modes.

The use of interfacing fluid 52 is not as an index matching layer per se, but as a "potential barrier" whose parameters can be used to control the strength of coupling of measuring light 62F between coupling prism 40 and substrate 20. In this manner, despite the large number of bounces per unit propagation length, the intensity of measuring light 62F coupled to a near-surface mode can be made to decay slower with propagation distance. This can allow for narrower and deeper (and thus sharper) coupling resonances than when an index-matching fluid is used. For that purpose, instead of selecting oil with an index higher than that of the measured modes, the interfacing fluid 53 having a refractive index that is lower than that of the measured modes, i.e., $n_f < n_{eff}$, is selected.

In an example embodiment, the thickness d1 of interfacing fluid 52 is at least as large as a threshold thickness $d1_{TH}$ that prevents over-coupling, limiting the error that would be caused by the high sensitivity of mode birefringence $B_m$ to the thickness d1. In particular, this method can rely on rejecting mode spectra lines 115TM and/or 115TE in which any of the coupling resonances of the modes, particularly of the low-order modes, are broader than a certain pre-defined value.

As noted above in connection with FIG. 3C, spectral lines 115TM and 115TE of the mode spectra have respective widths $W_{TM}$ and $W_{TE}$. In an example, widths $W_{TM}$ and $W_{TE}$ are measured at full-width at half-maximum (or full-width at half-minimum for dark-line resonances), wherein $W_{TM} < 0.0004$ RIU and $W_{TM} < 0.0004$ RIU, where RIU stands for refractive-index units that represent a variation in the corresponding effective index. In another example, $W_{TM} < 0.0002$ RIU and $W_{TM} < 0.0002$ RIU.

Figure 5:
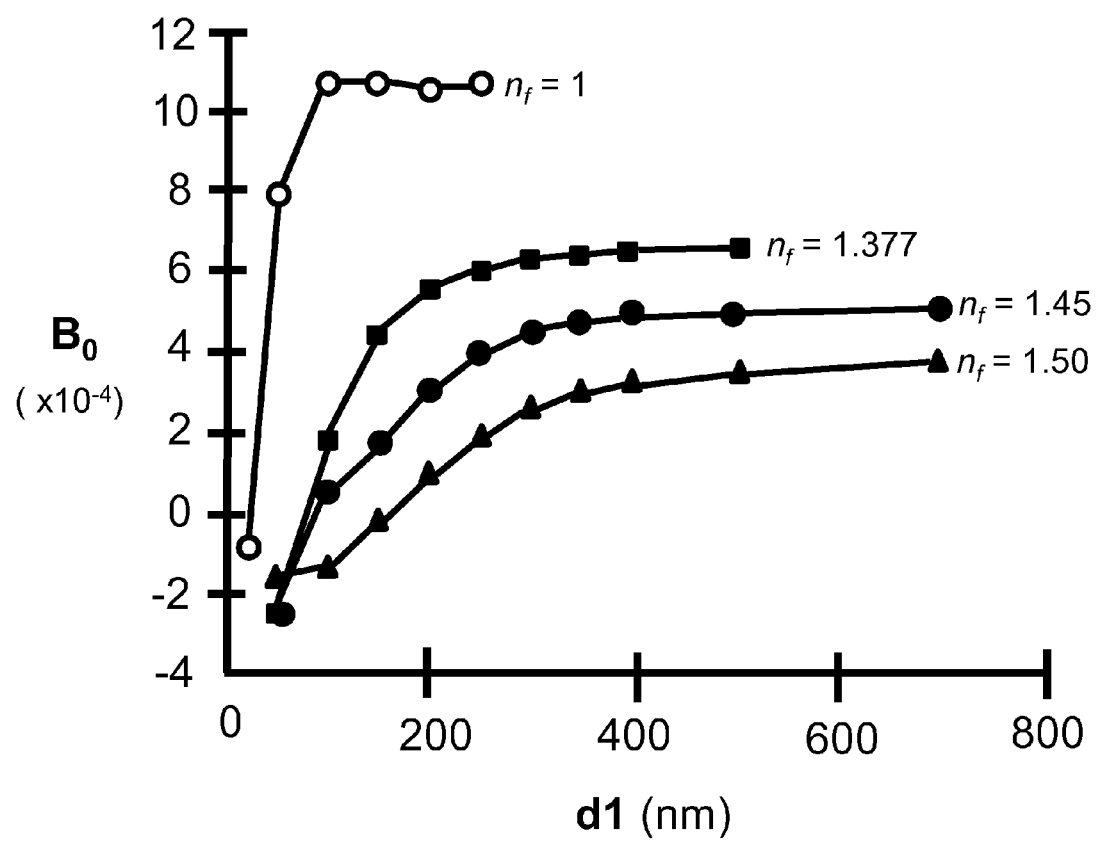
FIG. 5 is a plot, based on simulations, of the mode birefringence $B_0$ for the lowest-order (i.e., zero-order) TM and TE modes versus the thickness d1 (nm) of the interfacing fluid for different values of the refractive index $n_f$ of the interfacing fluid.

FIG. 5 is a plot based on numerical simulation of the thickness d1 (nm) of interfacing fluid 52 versus the lowest-order mode birefringence $B_0 = n_{eff}(TE_0) - n_{eff}(TM_0)$. The birefringence $B_0$ was calculated at λ=633 nm for the fundamental mode effective indices based on a shallow-$Ag^+$ ion-diffusion substrate, with the prism index $n_p$=1.72 and the substrate refractive index $n_s$=1.5. The theoretically formed waveguide was assumed to be stress-free to determine the mode birefringence induced specifically by the presence of interfacing fluid 52 and the proximity of coupling prism 40.

The plot of FIG. 5 shows how the mode birefringence for the lowest-order mode, induced by the surface boundary condition, depends on the thickness d1 for several different values of $n_f$ and over a range for d1. Each curve for $n_f$ has a corresponding thickness d1 beyond which the mode birefringence $B_0$ flattens out. This information can be used to establish the threshold thickness d1 $T_H$ that ensures the mode-spectra measurement is in a regime of low sensitivity of the mode birefringence to thickness d1 of interfacing fluid 52.

In an example, the threshold thickness d1 $T_H$ is where the mode birefringence B of one or both of the fundamental mode $B_0$ and the first-order mode $B_1$ are within 0.0002 RIU of their respective asymptotic values calculated for "infinite" thickness, e.g., a thickness many times larger than the optical wavelength. In another example, the threshold thickness d1 $T_H$ is where the mode birefringence $B_0$ of the fundamental mode and the mode birefringence $B_1$ of the first-order mode are both within 20% of their respective asymptotic values for thicknesses substantially larger than the wavelength of measuring light 62F. In another example, the threshold thickness d1 $T_H$ is selected to be approximately the thickness beyond which the mode birefringences $B_0$ and $B_1$ are within approximately $B_{tol}$, preferably within $0.7 B_{tol}$ of their asymptotic values, where $$B_{tol} \approx \frac{\Delta S}{SOC},$$

wherein $\Delta S$ is a desired precision of the estimate of surface stress, and SOC is the stress-optic coefficient.

In the regime where $B_0$ varies weakly with thickness d1, the intensity of reflected light 62R at angles below the critical angle ($n_{\textit{eff}} < n_s$) is typically greater than about 50% for TM-polarized light, and about 60% for TE-polarized light, for the simulated conditions involving prism with $n_p = 1.72$, and substrate with $n_s = 1.5$. The simulations assumed an infinitely large planar medium and infinitely large beam, so that reflection was total (100%) above the critical angle. The light intensity decays exponentially in the low-index medium.

In many real measurement conditions, illumination with measuring light 62F can generate significant amount of non-coupled parasitic background light that is detected by photodetector system 130 at angles within the range of the monitored angles $\beta_2$. This parasitic background light leads to reduction of the TM and TE mode spectra contrast. When such background is taken into account for real systems, the detected intensity at pixel positions corresponding to $n_{\textit{eff}} < n_s$ may be required to exceed 70%, 80%, or even 90% of the incident (or totally-reflected) intensity, to ensure adequate limiting of over-coupling to levels where the mode birefringence B induced by interfacing fluid 52 can properly be accounted for by treating it as a simple constant mode birefringence.

When thickness d1 is in the region of high sensitivity for mode birefringence B, the resonances of the low-order TM and TE modes confined to the steep and shallow index region R1 are substantially broadened compared to when d1 is in the region of low sensitivity. Hence, if the breadth of the coupling resonances is kept below a certain maximum acceptable value as described earlier, one can guarantee that the regime of low sensitivity is obtained, and the mode birefringence B can be easily accounted for when stress is calculated.

The variation in mode effective indices $n_{\textit{eff}}$ with thickness d1 is on the same order of the mode birefringence B, generally covering a range on the order of $10^{-4}$ or $10^{-3}$ for waveguides resulting from ion exchange in glasses, depending on the level of mode confinement near the top surface 22, and the index difference between the low-index interface medium, and the substrate surface. Larger ranges of mode index variation are possible, in particular with semiconductor substrates that have larger refractive indices than glass substrates. It is expected that the variation in mode effective indices $n_{\textit{eff}}$ with thickness d1 would be normally somewhat larger than the variation of the corresponding mode birefringence B.

There are practical ways of obtaining an appropriate thickness d1 of interfacing fluid 52. In an example, coupling surface 44 and substrate surface 22 are kept clean, or wiped clean shortly before being contacted. In one embodiment, the volume of interfacing fluid 52 necessary to obtain a uniform layer of the desired thickness d1 is calculated in advance, as the product of d1 and a contact area $A_P$ for coupling surface 44 of coupling prism 40. Then, the calculated volume of interfacing fluid 52 is applied to coupling surface 44 or substrate surface 22 using a pipette with precision volume control. Contact is then initiated between substrate surface 22 and coupling surface 44 of coupling prism 40. Surface tension forces help spread interfacing fluid 52 across the entire contact area. The application of a small amount of pressure can be used to help spread interfacing fluid 52.

In a related embodiment, an amount of interfacing fluid 52 larger than actually required is applied. The excess interfacing fluid is then squeezed out of the contact area by pressing or by sliding substrate 20 back and forth or in a circular or elliptical motion, until coupling of adequate contrast is observed for all modes, but while the intensity level for $n_{\textit{eff}} < n_s$ is still greater than the chosen lower limit, or while the breadth of all modes is still smaller than the desired upper limit.

Figure 6A:
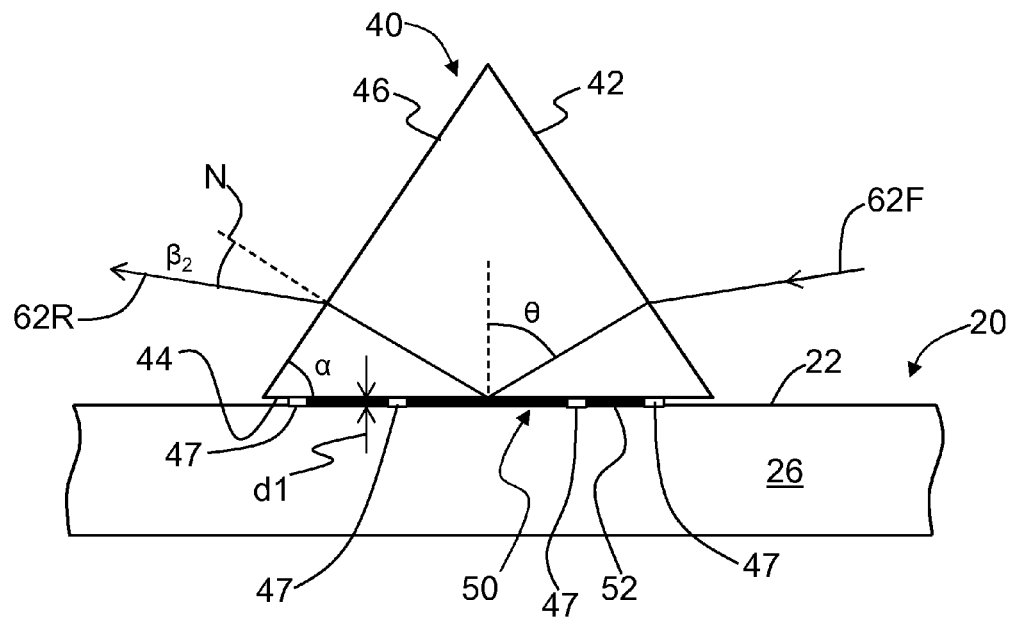
FIG. 6A is similar to FIG. 4A and illustrates an example wherein stand-off members ("stand offs") are used at the substrate-prism interface to define the thickness of the interfacing fluid.

FIG. 6A is similar to FIG. 4A and illustrates an embodiment wherein coupling surface 44 is provided with one or more stand-off members ("stand-offs") 47 having the thickness approximately equal to or greater than the smallest acceptable interface fluid thickness $d1_{TH}$ that provides a desired amount of insensitivity to mode birefringence. In an example, stand-offs 47 have dimensions preferably on the order of 1 mm$^2$ or smaller. Since contact is easily obtained on such small areas without application of significant pressure, when interfacing fluid 52 is applied between coupling prism 40 and substrate 20, stand-offs 47 define the thickness d1, which can be set to satisfy the condition $d1 > d1_{TH}$. Applying pressure or sliding the substrate squeezes out the excess interfacing fluid 52. More generally, stand-offs 47 define a thickness profile wherein d1 can either be constant or can vary as a function of position, as explained below.

In one version of this embodiment, stand-offs 47 are made of a low-index material, comparable to interfacing fluid index $n_f$. The smallness of stand-offs 47 relative to the total contact area $A_P$ of coupling surface 44 of coupling prism 40 ensures that the TM and TE mode spectra are not significantly altered if the refractive index of the stand-offs is significantly different from the index $n_f$ of the interfacing fluid and even if their refractive index is higher than the measured mode indices $n_{\textit{eff}}$. In an example, stand-offs 47 can be formed using photolithographic techniques. For example, a coating can be applied to prism-coupling surface 44, the coating selectively exposed, and then the exposed sections removed, thereby leaving a number of stand-offs 47. In other examples, a mask can be used to selectively etch a coating formed on coupling surface 44 of coupling prism 40, or selectively etch a desired prism-material thickness d1 from the prism coupling surface except for the masked stand-offs 47.

Figure 6B:
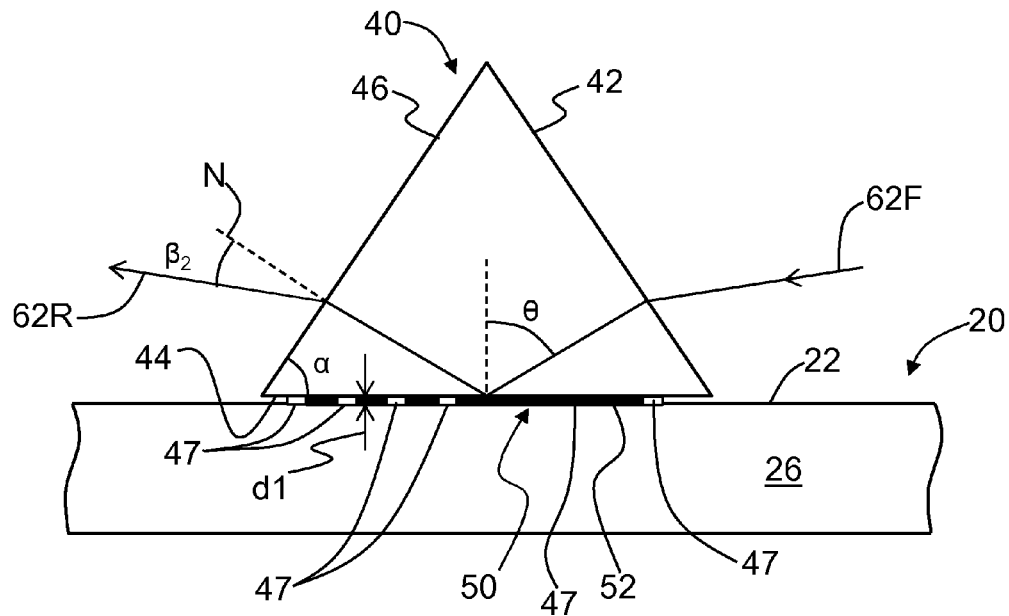
FIG. 6B is similar to FIG. 6A and illustrates an example where the stand-off members on the coupling surface are concentrated more toward the output surface side than toward the input surface side.

In another version of the same embodiment, one or more stand-offs 47 may be used on the side of the coupling surface 44 of the coupling prism 40 nearer to output surface 46 while no stand-offs or thinner stand-offs or fewer stand-offs may be applied near the input surface 42. FIG. 6B is similar to FIG. 6A and illustrates an example where the stand-offs 47 are more concentrated on the coupling surface closer to the output surface side than the input surface side. Such configurations serve to decreasing coupling strength along coupling surface 44 in the direction from input surface 42 to output surface 46 (i.e., from right to left in FIG. 6B). This can help improve the contrast of the measured mode spectra, particularly when combined with proper illumination.

Hence, stand-offs 47 can be used to control the thickness profile of interfacing fluid 52, and in particular can be used to define a thickness d1 that increases in the direction from input surface 42 to output surface 46. The thickness of the one or more stand-offs 47 can be selected in such a way that the range of thicknesses d1 of the interfacing fluid 52 is within the illuminated region of interface 50 from which reflected light 62R reflects and is collected by photodetector system 130 while remaining within the thickness range where the mode birefringence of the two lowest-order modes remains substantially unchanged to ensure accurate stress measurement.

In addition, the thickness d1 of interfacing fluid 52 may be defined relative to a median thickness $d1_m$ over the illuminated area, e.g., $(0.5) \cdot d1_m \le d1 \le (1.5) \cdot d2_m$. It is noted that in most if not all cases, if the mode birefringence of the fundamental mode remains substantially unchanged, so too will the mode birefringence of the next-highest-order mode.

Either the linewidth of the mode spectra or the coupling at angles below the critical angle can be used to ensure measurement in the region of stability. In an example, the full-width at half-minimum of the mode spectral lines 115TM and 115TE may be required to be <0.0004 RIU, or the angular spread of the mode spectra may be required to be below 0.05° after exiting from coupling prism 40 at output surface 46.

In another embodiment, over-coupling is prevented by ensuring that the bottoms of the intensity valleys of the mode spectra for the low-order modes are deeper than a certain percentage of the intensity in the immediately neighboring non-coupled regions of total-internal reflection in between. In an example, the intensity at the bottom of the intensity valleys are required to be 80% of the intensity of the immediately neighboring non-coupled regions of total-internal reflection.

In another embodiment, the amount of light 62 reflected at incident angles θ smaller than the critical angle $θ_C$ in the region of coupling to substrate radiation (non-bound) modes is monitored. In an example, light 62R reflected at angles smaller than the critical angle $θ_C$ by about 0.1° or more should be greater than about 50% of the incident light for TE polarization, and greater than about 50% of the incident light for TM polarization. In another example, light 62R reflected at angles smaller than the critical angle $θ_C$ by about 0.1° or more should be greater than about 60% of the incident light for TE polarization, and greater than about 60% of the incident light for TM.

Prism Coating

Figure 7A:
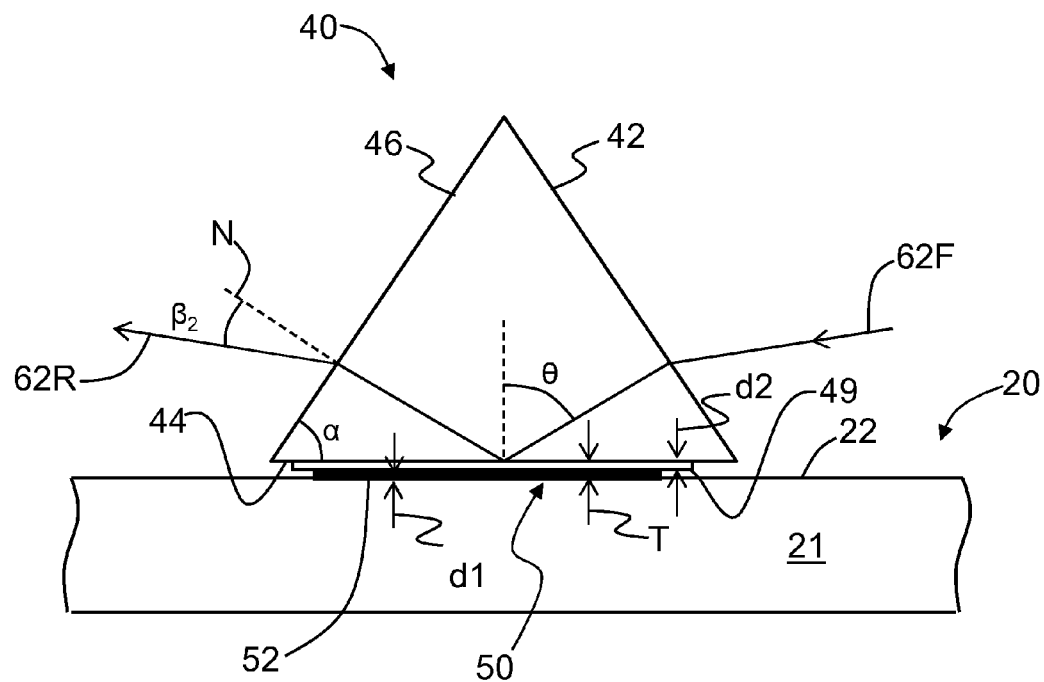
FIG. 7A is similar to FIG. 4A and FIG. 6A and illustrate an example wherein the coupling prism includes a prism coating on the coupling surface.

FIG. 7A is similar to FIG. 4A and FIG. 6A and illustrates an embodiment of system 10 wherein coupling prism 40 includes a low-index coating 49 ("prism coating") on coupling surface 44. Prism coating 49 has a thickness d2 and a refractive index $n_c$.

Figure 7B:
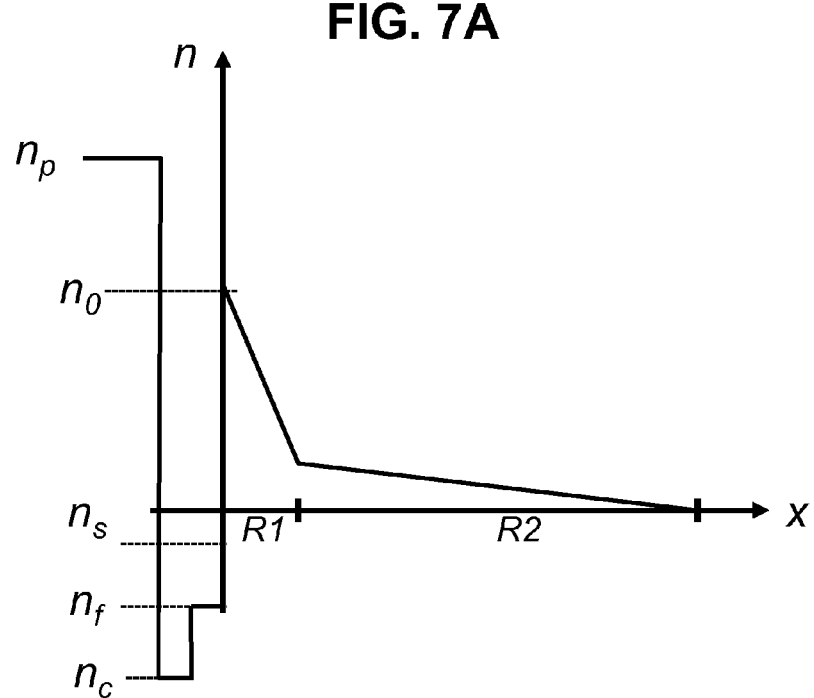
FIG. 7B is similar to FIG. 4B and plots the index profile n vs. distance x for the coupling prism, the prism coating, the interfacing fluid and the substrate.

FIG. 7B is similar to FIG. 4B and shows an example of the refractive index structure of the coupling prism 40, prism coating 49, interfacing fluid 52 and ion-exchanged substrate 20. In an example, coating index $n_c \le n_f \le n_{eff}$. Also in an example, $d2 \le d1_{TH}$. Prism coating 49 helps guarantee low sensitivity to mode birefringence B.

Figure 8:
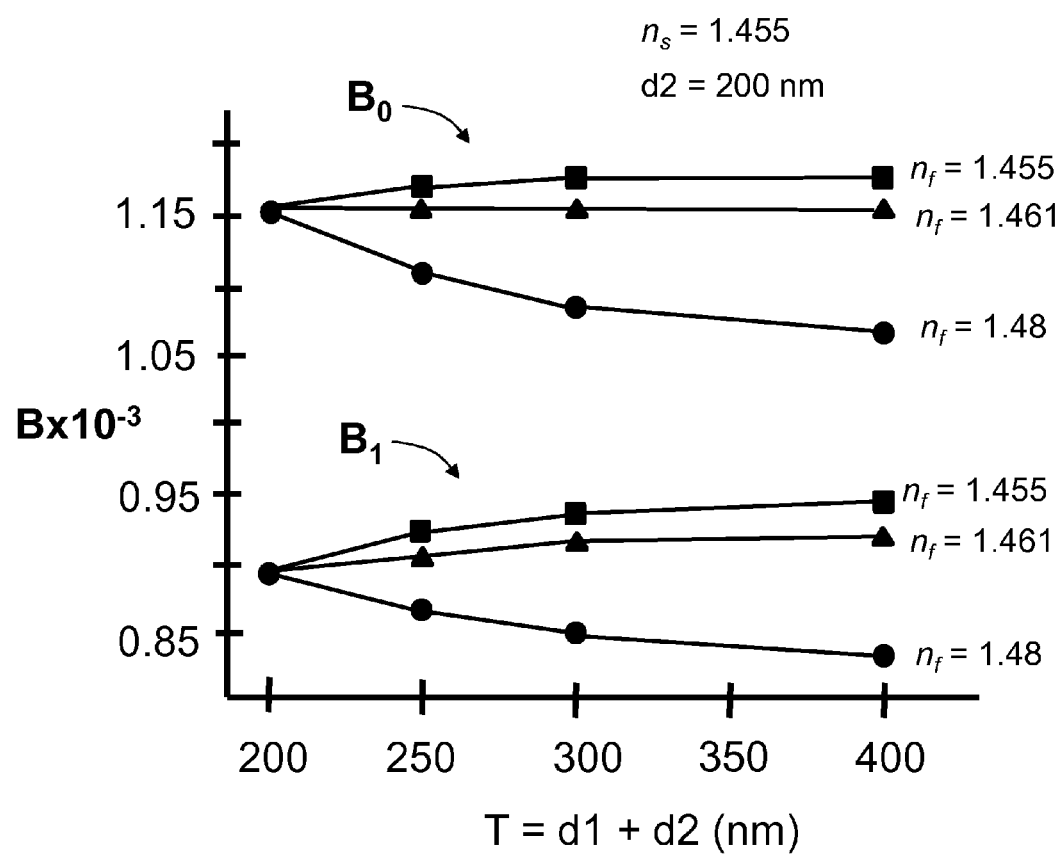
FIG. 8 is a plot similar to FIG. 5 and shows the mode birefringence B for the zero mode $B_0$ and first-order mode $B_1$, as a function of total thickness T (nm) for the prism coating (of thickness d2) and interfacing fluid (of thickness d1) for different values of the interfacing fluid refractive index $n_f$.

FIG. 8 is similar to FIG. 5 and plots the calculated mode birefringence B versus the total interface thickness $T = d1 + d2$ (nm) for the lowest-order mode ($B_0$) and the first-order mode ($B_1$) for three different values of $n_f$. The wavelength λ=405 nm, d2=200 nm, $n_c$=1.445, and $n_p$=1.72, and d1 is varied between 0 and 200 nm. The assumed depth D1 of the shallow steep region R1 is about 1 μm, and the surface index is about 1.6, such that two modes are confined mainly in region R1. The substrate index $n_s$ is assumed at about 1.525 at 405 nm.

From the plot of FIG. 8, it can be seen that the two curves for $n_f$=1.461 for the mode birefringence B for the two lowest-order modes are relatively constant over the entire range of total thicknesses T from 200 to 400, or over the range of thickness d1 from 0 to 200 nm. It can be expected that for this example, if $n_f$ is between about 1.46 and about 1.465, the variation of mode birefringence B for each of the two lowest-order modes would be less than about $5 \times 10^{-5}$ RIU, corresponding to a stress variation of about 15 MPa. The estimate of the surface birefringence then would be accurate to better than 30 MPa (i.e., 30 MPa or less). In all three examples in FIG. 8, for $B_0$ and $B_1$ the variation B' in the mode birefringence B is below $1 \times 10^{-4}$ over the entire range of d1. This represents at least a 7-fold reduction of variation as compared to the case for $n_f \approx 1.45$ without the use of prism coating 49, as can be seen by comparing to FIG. 5.

In another example, prism coating 49 is made of $SiO_2$ with d2=185 nm and $n_c \approx 1.441$ at 488 nm and is applied to coupling surface 44 of a coupling prism 40 having $n_p \approx 1.73$ at 488 nm, and combined with an interfacing oil 52 having $n_f \approx 1.487$ at 488 nm. This example configuration allows easy coupling while limiting the variation of coupling-configuration-related mode birefringence to a tolerable level. In other examples, prism coating 49 may be made of $CaF_2$, $MgF_2$, or other materials, which upon evaporation or sputtering, form thin films with refractive indices $n_c$ lower than that of the substrates to be measured.

It is useful to have thickness d2 of prism coating 49 be at or near its optimum value for good coupling while also limiting the error in birefringence B in combination with interfacing fluid 52 of thickness d1. In an example, the optimum thickness d2 is when the optical path $n_c \cdot d2$ satisfies the criterion $0.2λ \le n_c \cdot d2 \le 0.82$, where λ is the vacuum wavelength of light used to make the mode spectra measurement. If the near-surface region of the index profile is particularly steep, such as $$\left| \frac{\lambda}{n} \frac{dn}{dx} \right| \ge 0.0008,$$

the optimum thickness d2 may be found in the narrower range $0.45λ \le n_c \cdot d2 \le 0.8λ$.

In another example, $0.52λ \le n_c \cdot d2 < 0.72$. The optimum value for $n_f$ is between $n_c$ and $n_{eff}$, and in an example, $n_c + 0.15(n_{eff} - n_c) \le n_f \le n_c + 0.30(n_{eff} - n_c)$, with $n_{eff}$ representing in this particular case a typical index in the range of the two lowest-order modes whose exact effective indices may not be known in advance. If the quantity $n_c + 0.30(n_{eff} - n_c)$ is higher than the effective index of the lowest-order mode of the spectrum that is required to be measured, then $n_f$ may be chosen to be slightly lower than the index of the lowest-order mode. In an example, $n_f = n_s$, or slightly lower than $n_s$, such as lower by no more than 0.01 of $n_s$, i.e., $(0.99) \cdot n_s \le n_f \le n_s$.

Stabilizing the mode birefringence B associated with the presence of prism coating 49 is very helpful when applying various routines for obtaining the TM and TE index profiles (and from them, the stress profile and birefringence) using the measured TM and TE mode spectra. For example, when the mode birefringence B is stabilized, then interfacing fluid 52, prism coating 49, and coupling prism 40 can be modeled as a single, semi-infinite medium with an index equal to or very close to $n_f$. This can significantly simplify the measurement algorithms used to calculate the TM and TE index profiles.

In an example embodiment, refractive index $n_f$ of interfacing fluid 52 is selected to minimize or reduce to acceptable level the variation of mode birefringence B for the zero and first-order modes (i.e., the first two lowest-order modes), that is, $B_0$ and $B_1$. In an example, $n_f$ is selected such that when increasing the thickness d1 from 0 to larger values, the mode birefringences $B_0$ and $B_1$ change in opposite directions.

In another example, $n_f$ is selected such that the variation of mode birefringence B for each of the modes with thickness d1 is less than a desired fraction of the variation when $n_f=n_c$, e.g., $$|B(d1=0,n_f)-B(d1\gg\lambda,n_f)|<F\times|B(d1=0,n_f=n_c)-B(d1\gg\lambda,n_f=n_c)|$$

where the fraction factor F may be equal to or smaller than 0.5 as an example, indicating a significant improvement in mode birefringence stability as a result of selecting a fluid index $n_f$ different from the coating index $n_c$.

In another embodiment, the thickness d2 of prism coating 49 may vary from thinner near the edge of coupling prism 40 at input surface 42 to thicker near the edge of the coupling prism at output surface 46. This configuration serves to vary the coupling strength along the coupling surface 44, with decreasing strength in the direction from the input surface 42 to the output surface 46. This makes it easier to arrange the illumination of measuring light 62F to obtain high-contrast TM and TE mode spectra for the coupling resonances of all modes. In an example, the variation of the thickness d2 of coating 49 over the illuminated area of interface 52 may vary over a range that is related to a median thickness $d2_m$ of the coating, i.e., $(0.5)\cdot d2_m \leq d2 \leq (1.5)\cdot d2_m$.

In another embodiment, the prism coating 49 may be combined with one or more stand-offs 47 on the prism coupling surface 44. In an example, the stand-offs 47 may be situated closer to the output surface 46 to create an increasing thickness d1 of interfacing fluid 52. This can serve to decreasing the coupling strength of measuring light 62F in the direction from input surface 42 to output surface 46, making it easier to obtain illumination conditions that support high-contrast TM and TE mode spectra.

Detecting the Mode Spectra

With reference again to FIG. 3B, in an example embodiment, detector 110 of photodetector system 130 has more than about 1400 pixels per row or column, such that the angular distribution of intensity collected during mode spectra measurements using system 10 is spread over at least 1400 data points. In another example, detector 110 has more than about 3000 pixels per row or column. This allows for simultaneous high-resolution measurement in a single captured digital image of both the high-density TM and TE mode spectra that are spatially spread over the deep, low-index region R2 of the index profile, and the low-density mode spectra confined to the steep, often shallow, near-surface region R1 of the index profile. In an experiment, an example detector 110 with 5184 columns of pixels was used to capture wide-$n_{eff}$-range, high-resolution prism-coupling TM and TE spectra of ion-exchanged substrates 20 made using a first ion exchange performed in $KNO_3$ bath, and second, shallower ion exchange performed in baths containing various mixtures of $KNO_3$ and $AgNO_3$, including baths containing pure $AgNO_3$.

As mentioned above, when relatively wide-angular spectra are collected (for example, greater than about 5°), the approximation of a linear relationship between the mode spectral line spacing at detector 110 and the difference in effective indices $n_{eff}$ of the modes corresponding to the spectral lines may no longer have adequate accuracy and can lead to unacceptable distortions of the calculated index and stress profiles. For such cases, the methods disclosed herein include employing exact relationships between the locations of TM and TE spectral lines 115TM and 115TE on the sensor plane for the TM and TE mode spectra and the effective indices $n_{eff}$ to ensure measurements of maximum accuracy. Such use of an exact relationship between spectral line location and effective index becomes even more important when the angular sensitivity $$\frac{d\beta_2}{dn_{eff}}$$

is significant, such as greater than about 3, since such cases usually involve coupling prisms 40 with a prism index $n_p$ relatively close to the substrate index $n_s$, and the angular sensitivity itself changes relatively fast with effective index. Thus, using a single value of $$\frac{d\beta_2}{dn_{eff}}$$

for a relatively large range of $n_{eff}$ would lead to potentially significant and undesired distortions of the extracted index and stress profiles.

In particular, with reference again to FIG. 3A, when detector 110 coincides with the focal plane 92 of the collection optical system 90, and optical axis A2 is normal to photosensitive surface 112 and the plane of an ideal lens that can represent the optical system 90, then the following relationship holds:

$$\beta_2^{center} = \sin^{-1}\left(n_p \sin\left(\sin^{-1}\left(\frac{n_{center}}{n_p}\right) - \alpha\right)\right)$$

where $\beta_2^{center}$ is the exit angle (with respect to the normal N to the prism exit surface 46) that corresponds to an effective index that is mapped onto an imaginary spectral line passing through the center of the photosensitive surface 112 of detector 110.

Then the effective index corresponding to a position x on photosensitive surface 112 can be found from the equation $$n_{eff}(x) = \sin\left\{\alpha + \sin^{-1}\left[\frac{1}{n_p}\sin\left(\beta_2^{center} + \tan^{-1}\left(\frac{x - x_{center}}{f}\right)\right)\right]\right\}$$

where f is the focal length of the collection optical system 90, and $x_{center}$ is the position of the pixel column corresponding to the center of photosensitive surface 112, through which the optical axis A2 passes. More generally, if the optical axis A2 crosses photosensitive surface 112 other than at the center, the angle $\beta_2^{center}$ is taken to correspond to a more generalized location $x_{center}$ that represents the location where the optical axis A2 intersects the photosensitive surface.

One convenient way to use the above relationships is to calibrate the value of $n_{center}$ or $\beta_2^{center}$ by measuring a material of known refractive index, and adjusting $n_{center}$ or $\beta_2^{center}$ until the last equation reproduces the measured index. After that, as long as the optical system 90 is kept fixed, the same value of $n_{center}$ (or $\beta_2^{center}$) to convert any x to a corresponding $n_{eff}$.

It will be apparent to those skilled in the art that various modifications to the preferred embodiments of the disclosure as described herein can be made without departing from the spirit or scope of the disclosure as defined in the appended claims. Thus, the disclosure covers the modifications and variations provided they come within the scope of the appended claims and the equivalents thereto.

What is claimed is:

1. A method of measuring TM and TE mode spectra of an ion-exchanged glass substrate having a bulk refractive index $n_s$, a surface, a refractive index profile n as a function of depth x below the surface, and a near-surface region R1, comprising:
   interfacing a coupling prism of refractive index $n_p$ to the substrate surface to define a prism-substrate interface, with an interfacing fluid of refractive index $n_f$ and thickness d1 residing between the coupling prism and substrate surface, wherein $n_f \leq n_s < n_p$, wherein region R1 satisfies $$\left| \frac{\lambda}{n} \frac{dn}{dx} \right| \geq 0.0004,$$

wherein λ is a measurement wavelength of measuring light; and
   directing the measuring light through the coupling prism and through the interfacing fluid into the substrate surface and digitally capturing TE and TM mode spectra reflected from the prism-substrate interface, wherein the TM and TE mode spectra each include first and second lowest-order modes, and thickness d1 is within a range such that that a mode birefringence of at least the first and second lowest-order modes of the TE and TM spectra as measured in the presence of the coupling prism remains substantially unchanged within the range.

2. The method of claim 1, further comprising providing one or more stand-off members on at least one of the coupling surface of the coupling prism and the substrate surface to define the thickness d1.

3. The method of claim 1, wherein the coupling prism includes a coupling surface having a coating, wherein the coating comprises a coating thickness d2 and a coating refractive index $n_c$, wherein $n_c \leq n_f$.

4. The method of claim 3, wherein the coating thickness d2 and the coating refractive index $n_c$ satisfy $0.2\lambda \leq n_c \cdot d2 \leq 0.8\lambda$.

5. The method of claim 3, wherein at least one of the interfacing fluid thickness d1 and the coating thickness d2 is constant as a function of position.

6. The method of claim 3, wherein $n_c + 0.15(n_{eff}^t - n_c) \leq n_f \leq n_c + 0.30(n_{eff}^t - n_c)$, where $n_{eff}^t$ represents a middle of a target range of an effective index $n_{eff}$ where lowest-order modes of the TE and TM mode spectra are expected to occur.

7. The method of claim 3, wherein $(n_s - 0.01) \leq n_f \leq n_s$.

8. The method of claim 3, wherein the prism coating comprises $SiO_2$, $CaF_2$, or $MgF_2$.

9. The method of claim 1, wherein the interfacing fluid has a median thickness $d1_m$, and wherein $(0.5) \cdot d1_m \leq d1 \leq (1.5) \cdot d1_m$ at all positions in the area illuminated by the measuring light.

10. A method of measuring TM and TE mode spectra of an ion-exchanged glass substrate having a bulk refractive index $n_s$, a surface, a refractive index profile n as a function of depth x below the surface, and with a near-surface region R1, comprising:
    interfacing a coupling prism of refractive index $n_p$ to the substrate surface to define a prism-substrate interface, with the coupling prism having a coupling surface with a coating, the coating having a coating thickness d2 and a coating refractive index $n_c$ wherein $0.2\lambda \leq n_c \cdot d2 \leq 0.8\lambda$;
    providing an interfacing fluid of refractive index $n_f$ and thickness d1 between the prism coating and substrate surface, wherein $n_c \leq n_f \leq n_s < n_p$, wherein region R1 satisfies $$\left| \frac{\lambda}{n} \frac{dn}{dx} \right| \geq 0.0004,$$

wherein λ is a measurement wavelength of measuring light; and
    directing the measuring light through the coupling prism and through the interfacing fluid into the substrate surface and digitally capturing the TE and TM mode spectra reflected from the prism-substrate interface.

11. The method according to claim 10, further comprising selecting indices $n_c$ and $n_f$ and coating thickness d2 such that a variation of mode birefringence $\Delta B \leq B_{tol}$ for at least first and second lowest-order modes for each of the TM and TE mode spectra, where $B_{tol}$ is a tolerance on the variation in the mode birefringence.

12. The method of claim 10, wherein the coating thickness d2 and the coating refractive index $n_c$ satisfy $0.45\lambda \leq n_c \cdot d2 \leq 0.8\lambda$.

13. The method of claim 10, wherein $n_c + 0.15(n_{eff}^t - n_c) \leq n_f \leq n_c + 0.30(n_{eff}^t - n_c)$ where $n_{eff}^t$ represents a middle of a target range of an effective index $n_{eff}$ where lowest-order modes of the TE and TM mode spectra are expected to occur.

14. The method according to claim 10, wherein the glass substrate includes in-diffused K+ and Ag+ ions.

* * * * *

UNITED STATES PATENT AND TRADEMARK OFFICE
CERTIFICATE OF CORRECTION

PATENT NO. : 9,983,064 B2
APPLICATION NO. : 14/523171
DATED : May 29, 2018
INVENTOR(S) : Rostislav Vatchev Roussev et al.

Page 1 of 1

It is certified that error appears in the above-identified patent and that said Letters Patent is hereby corrected as shown below:

On the Title Page

On page 2, Column 1, item (56), U.S. Patent Documents, Line 23, delete "Manley" and insert -- Manlay --, therefor.

On page 2, Column 2, item (56), other publications, Line 34, delete "Agricultrual" and insert -- Agricultural --, therefor.

In the Claims

In Column 17, Line 37, Claim 1, delete "that that" and insert -- that --, therefor.

Signed and Sealed this
Twenty-sixth Day of May, 2020

Andrei Iancu
*Director of the United States Patent and Trademark Office*